United States Patent
Moldt et al.

(10) Patent No.: US 9,470,621 B2
(45) Date of Patent: Oct. 18, 2016

(54) MODIFIED MEASURING CUVETTE

(71) Applicant: Dräger Safety AG & Co. KGaA, Lübeck (DE)

(72) Inventors: Andreas Moldt, Pittsburgh, PA (US); Andrea Baumeister, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 14/594,413

(22) Filed: Jan. 12, 2015

(65) Prior Publication Data

US 2015/0198521 A1    Jul. 16, 2015

(30) Foreign Application Priority Data

Jan. 14, 2014  (DE) ........................ 10 2014 000 210

(51) Int. Cl.
| | |
|---|---|
| *G01N 1/10* | (2006.01) |
| *G01N 21/03* | (2006.01) |
| *G01N 21/15* | (2006.01) |
| *G01N 21/05* | (2006.01) |
| *G01N 21/3504* | (2014.01) |

(52) U.S. Cl.
CPC .............. *G01N 21/03* (2013.01); *G01N 21/05* (2013.01); *G01N 21/15* (2013.01); *G01N 21/3504* (2013.01); *G01N 2021/0389* (2013.01)

(58) Field of Classification Search
CPC ............. G01N 33/5088; G01N 33/60; G01N 2500/00; G01N 2800/042; G01N 2800/044; G01N 2800/323; G01N 33/5008; G01N 33/5011; G01N 33/5014; G01N 33/5038; G01N 33/58; G01N 33/6881; G01N 33/6887
See application file for complete search history.

(56) References Cited

U.S. PATENT DOCUMENTS

| | | | |
|---|---|---|---|
| 3,614,243 A * | 10/1971 | Harvey | G01N 21/0303 250/429 |
| 3,936,196 A | 2/1976 | Wickersheim | |
| 4,268,478 A | 5/1981 | Huber | |
| 5,204,270 A * | 4/1993 | LaCount | G01N 21/3504 250/343 |
| 5,616,923 A | 4/1997 | Rich et al. | |
| 6,254,828 B1 * | 7/2001 | LaCount | G01N 21/3504 250/343 |
| 7,576,841 B2 | 8/2009 | Sasayama | |
| 2002/0029003 A1 | 3/2002 | Mace et al. | |

FOREIGN PATENT DOCUMENTS

| | | |
|---|---|---|
| CN | 201697875 U | 1/2011 |
| DE | 42 115 A1 | 10/1965 |
| DE | 195 43 105 A1 | 5/1997 |
| DE | 195 43 105 C2 | 9/1998 |
| DE | 20022379 * | 8/2001 |
| DE | 102 47 272 A1 | 4/2004 |
| DE | 10 2009 027 136 A1 | 12/2010 |
| EP | 0 596 605 A1 | 5/1994 |
| EP | 1 383 428 B1 | 12/2010 |

OTHER PUBLICATIONS

British Examination Report dated Feb. 29, 2016.

* cited by examiner

*Primary Examiner* — Michael P Stafira
(74) *Attorney, Agent, or Firm* — McGlew and Tuttle, P.C.

(57) ABSTRACT

A measuring cuvette (1), for the spectroscopic analysis of a gas sample in a ray path between a radiation source and a detector, preferably suitable for use in a gas-measuring device (19), has a vessel wall (2) that at least partially encloses a sample space (3) for receiving a process gas. At least one window element (4), through which electromagnetic radiation can be coupled into the sample space (3) from the outside, is indirectly or directly connected with the vessel wall (2). An inlet as well as an outlet (5) are included, through which the process gas can be introduced into the sample space (3) and can be removed from the sample space (3). At least one fastening element (6) makes possible both secure fastening of the window element (4) on the vessel wall (2) and separation of the window element (4) from the vessel wall (2) without destruction.

20 Claims, 6 Drawing Sheets

MODIFIED MEASURING CUVETTE

CROSS REFERENCE TO RELATED APPLICATIONS

This application claims the benefit of priority under 35 U.S.C. §119 of German Patent Application DE 102014000210.1 filed Jan. 14, 2014, the entire contents of which are incorporated herein by reference.

FIELD OF THE INVENTION

The present invention pertains to a measuring cuvette for the spectroscopic analysis of a gas sample arranged in the ray path between a radiation source and a detector. The measuring cuvette described, which is preferably suitable for use in a gas-measuring device, especially in a so-called gas detector, has a vessel wall, which encloses at least partially a sample space for receiving a process gas, at least one window element, through which the electromagnetic radiation can be coupled from the outside into the sample space and which is indirectly or directly connected with the vessel wall, and an inlet as well as an outlet, through which the process gas can be introduced into the sample space and removed from the sample space.

BACKGROUND OF THE INVENTION

Measuring cuvettes of this class are used above all for stationary gas-measuring devices, especially so-called gas detectors, with which plants intended for the delivery and processing of combustible substances are secured. Such stationary gas-measuring devices usually measure the local gas concentration at the site of installation of the device. If these gas-measuring devices are used to monitor a process gas present in a closed process or to monitor the gas concentration at a certain point (so-called point detection), they usually have a measuring cuvette, through which the process gas to be analyzed is specifically sent.

To guarantee the monitoring of gas concentrations in closed processes, the process gas to be analyzed is first removed in these cases from the process proper and then introduced into the measuring cuvette. A suitable tubing or hose line, which is fastened at special ports of the measuring cuvette, is used for feeding and removing the process gas.

If a measuring cuvette of this class is used in a gas-measuring device, this device has a mount, within which the measuring cuvette is positioned and fixed. Such a gas-measuring device, especially gas detector, usually has, furthermore, at least one radiation source as well as a detector, between which the ray path with the measuring cuvette arranged is located. In any case, the measuring cuvette is arranged in the optical path between the radiation source and the optical detector such that the emitted radiation passes through the process gas when passing through the measuring cuvette. After the radiation has passed through the sample space of the measuring cuvette for the first time, it usually falls on a reflector element, especially a mirror, is reflected here in the direction of the measuring cuvette and passes through the sample space in an at least nearly opposite direction for a second time. Since the sample space of the measuring cuvette is passed through by the light beam twice, the effective length of the measuring section is doubled and more accurate measurement is thus made possible.

While the radiation, whose wavelength is often in the infrared range, is passing through the sample space of the measuring cuvette filled with process gas, the property, especially the intensity and/or wavelength, of the radiation changes because of a partial absorption of the radiation by the process gas. After passing through the sample space of the measuring cuvette, the radiation is focused on a radiation detector in a suitable manner and the detected radiation is analyzed based on a comparison with the radiation emitted originally.

A corresponding optical gas analyzer with a pyroelectric detector element is known from DE 195 43 105 C2. The gas analyzer has a sensor, which determines the percentage of special gas components in a gas sample based on an analysis of the absorption of infrared radiation in the sample gas. The technical solution described is characterized above all by a special mounting of the detector, which embodies a preferred elastic mounting based on the use of an elastomer. An advantageous vibration decoupling and, as a result, broadband analyzability of the measured signal are made possible based on the special mounting.

Furthermore, a spectroscopic sensor, in which the infrared radiation source and the detector are fastened and contacted on a circuit board, e.g., a printed circuit board, is known from DE 10 2009 027 136 A1. The absorption section is designed here as an interior space of a cylindrical reflector device, which is likewise fastened to the circuit board and has a reflecting inner surface. Direct transmission of radiation from the infrared radiation source to the detector, i.e., without reflection at the reflector device, is prevented by means of a diaphragm provided herefor. Thus, the sensor described is characterized in that the reflector is located within the sample chamber of the measuring cuvette.

It is common to all prior-art measuring cuvettes that these have a sample space for the process gas to be measured as well as at least one window element, via which the electromagnetic radiation is coupled into the sample space from a radiation source. To obtain the longest possible measuring section within the sample space filled with the process gas to be monitored, suitable reflector devices are provided either within the sample space or outside thereof. The prior-art measuring cuvettes thus enclose a defined gas volume and have optical accesses in order to make it possible for the electromagnetic radiation emitted by the radiation source to pass through the gas to be analyzed. The optical accesses become contaminated during the operation due to dirt particles present in the ambient air or in the gas to be analyzed. This leads to losses of signal and compromises the measurement of the gas.

The optically transparent element is permanently bonded into the measuring cuvette in the prior-art measuring cuvettes. This compromises the accessibility and thus makes it difficult to clean the optical accesses. Since sapphire disks are often arranged in the optical accesses, replacing the measuring cuvette in question solely because of contamination is, furthermore, undesired.

SUMMARY OF THE INVENTION

Based on the prior-art measuring cuvettes and the problem described above, a basic object of the present invention is to further improve a measuring cuvette such that contaminants present at the optical accesses, especially at the window elements arranged here, can be removed easily and without major effort. Besides improved accessibility to the optical accesses, the necessary tightness must be ensured at the same time in these areas. In particular, the tightness of the sample space in the interior of the measuring cuvette is of crucial significance during the measurement being performed. Since the sample space of the measuring cuvette contains the gas to be measured, ambient gases must be reliably prevented from entering the interior of the measuring cuvette both under ambient pressure and under vacuum and overpressure in the interior of the cuvette. It shall, furthermore, be borne in mind in this connection that the permanent bonding of the disks used as window elements at the optical inlets of the measuring cuvette, which bonding has hitherto been usually provided, has only a very limited ability to withstand a vacuum in the sample gas space. Sealing of the measuring cuvette against the ambient gases both in the direction of the radiation source and in the direction of a reflector arranged outside the measuring cuvette also must be guaranteed at any time. Since such measuring cuvettes are often used in gas-measuring devices, especially in so-called gas detectors, with corresponding mounts, the technical solution according to the present invention shall, furthermore, preferably ensure that length tolerances in the surrounding components of the vessel wall, in which especially the radiation source and/or a reflector element are arranged, can be compensated. A corresponding length compensation shall be able to be achieved by means of simple technical steps. At the same time, the measuring section within the measuring cuvette must not be changed, especially not shortened. The technical solution to be described shall be embodied with comparatively simple means and in a cost-effective manner.

The present invention is based on a measuring cuvette for the spectroscopic analysis of a sample, which is arranged in the ray path between a radiation source and a detector, which said measuring cuvette has a vessel wall, which at least partially encloses a sample space for receiving a process gas, at least one window element, through which electromagnetic radiation can be coupled into the sample space from the outside and which is indirectly or directly connected with the vessel wall, and an inlet as well as an outlet, through which inlet and outlet a process gas can be introduced into the sample space and removed from the sample space. The measuring cuvette is improved according to the present invention by the provision of a fastening element, which makes possible both the secure fastening of the window element on the vessel wall and nondestructive separation of the window element from the vessel wall. A measuring cuvette designed according to the present invention is thus characterized above all in that at least one window element is provided, which can be removed from the measuring cuvette without destruction and can thus be cleaned in a simple manner. After completion of the cleaning, the window element can again be fastened to the housing wall of the measuring cuvette by means of a fastening element designed according to the present invention, which may have a screw, flap and/or tensioning mechanism.

Thus, an opening in the housing wall is sealingly covered with the window element during the operation of the measuring cuvette, and the window element is transparent to electromagnetic radiation, especially to light in the infrared range. The measuring cuvette is designed here such that light emitted by a radiation source enters the sample space, passes through the sample space preferably in the longitudinal direction, is subsequently reflected from a reflector and again passes through the sample space in the longitudinal direction before the radiation falls on a detector and is analyzed.

With respect to the reflector element used preferably, it is conceivable, in principle, to arrange this within or outside the sample chamber.

The window element is preferably designed as a sapphire disk. Based on the technical solution according to the present invention, which provides for a fastening device for the detachably rigid fastening of the window element on the vessel wall of the measuring cuvette, it is now possible in a simple manner to separate a contaminated sapphire disk from the measuring cuvette, to clean it and to subsequently fasten it again on the measuring cuvette. To guarantee sufficient tightness of the sample space against the surrounding area, at least one sealing element is provided between the window element and the vessel wall in the mounted state according to a special variant of the present invention. This is preferably a packing ring or a sealing washer, which is clamped between the window element and a sealing surface of the vessel wall, which sealing surface is provided for this, by means of the fastening element. In any case, the sealing is brought about in such a manner that the sample space is sealed gas-tightly against the area surrounding the measuring cuvette.

The fastening element preferably has an opening, through which the radiation can pass unhindered, especially in order to be able to fall on the window element fixed by the fastening element and to finally pass through it. Such a passage opening is preferably a recess in the interior of the fastening element, in which case the basic body of the fastening element is preferably ring-shaped.

According to a special embodiment of the present invention, the sample space of the measuring cuvette surrounding the vessel wall has an opening on one side, while the window element fastened by means of the fastening element provided according to the present invention is arranged on a side of the measuring cuvette located opposite that side. The sample chamber of the measuring cuvette is thus half open in this case. A measuring cuvette having such a design can be preferably connected with the side towards which the sample chamber is open with a device for gas measurement, which has a radiation source. The measuring cuvette is preferably connected with the device for measuring the gas such that, on the one hand, radiation can enter the sample space unhindered through the opening and, on the other hand, reliable sealing of the sample space or of the opening against the surrounding area is ensured. To guarantee this, the housing wall of the measuring cuvette has, on the side on which the opening is provided, a stop face with a sealing surface, for which a suitable sealant is provided, which is pressed against a contact surface of the device for measuring the gas as soon as the measuring cuvette is located in the cuvette mount of the device in the mounted state.

If radiation originating from the radiation source passes through the opening into the sample chamber, the radiation preferably passes through the sample chamber in the direction of the longest extension thereof. On the opposite side, the radiation falls on the window element that is optically at least partially transparent to it, leaves the sample chamber as a result, and is reflected on a reflector arranged outside the measuring cuvette, reenters the sample chamber through the window element of the measuring cuvette and finally reaches the detector likewise arranged in the device for the gas measurement.

According to an especially advantageous embodiment, the measuring cuvette designed according to the present invention is now fixed between the device with radiation source for gas measurement, especially a gas-measuring device or a so-called gas detector, and a bracket, to which a reflector is fastened. To compensate any possible length tolerances between the device with the radiation source and the bracket, a measuring cuvette designed according to the present invention, especially the fastening element, preferably has an adjusting element for height or length adjustment. A distance between a stop face of the cuvette housing, which faces the device with the radiation source, and a stop face located opposite, which faces the bracket, which preferably has a reflector, can be varied by means of this adjusting element. Reliable fixation of the measuring cuvette within a gas-measuring device is possible in this manner despite the length tolerances existing in this device. In particular, a locking element, especially a locknut, which is designed such that loosening of the fastening element and hence of the window element is reliably prevented from occurring when this locking element is actuated to increase the distance between the two stop faces, i.e., when the effective length of the measuring cuvette is increased.

It is conceivable according to a special variant of the present invention that the fastening element has a clamp and/or a clamping element. It appears to be especially suitable, furthermore, for the fastening element to have at least one thread. In a special embodiment, the fastening element therefore has at least a screw cap, which can be screwed on an external thread provided on the vessel wall. Furthermore, provisions are preferably made for a sealing washer or a packing ring to be arranged between the screw cap and the window element in the mounted state of the window element. By tightening the screw cap, the window element is pressed in the direction of the vessel wall and the sealing element provided between the window element and the vessel wall is clamped in at the same time.

The vessel wall, on which at least one inlet as well as an outlet each are provided for the process gas, has, in particular, a cylindrical shape, and the radiation passes through the measuring cuvette in the longitudinal direction. The longest possible measuring section shall be provided in this manner and especially reliable gas measurement shall thus be guaranteed.

According to the present invention, a preferred use of the measuring cuvette described pertains to the use in a gas-measuring device, especially in a stationary gas-measuring device or so-called gas detector, as it is frequently used in the chemical and petrochemical industry. According to a special variant of the present invention, the measuring cuvette is fixed between a housing, in which at least one radiation source is arranged, and a bracket. Furthermore, it is conceivable, in particular, that a reflection device, especially a mirror, is fixed on the bracket, so that radiation leaving the sample space is reflected at least partially in the direction of the sample space.

A measuring cuvette, which is open on one side and is fastened by means of a suitable bracket on a device having a radiation source and detector, is preferably used. However, it is also conceivable, in principle, to equip a measuring cuvette for analyzing a process gas with two window elements arranged opposite each other, which are in turn preferably fastened each on the vessel wall by means of a fastening element, so that the window elements can be separated from the vessel wall, cleaned and subsequently fastened again on the vessel wall as needed, especially in case of heavy contamination. To guarantee reliable sealing of the sample space against the surrounding area, sealing elements, especially packing rings or sealing washers, are provided between the window elements and the vessel wall in this case as well. A screw cap, which is screwed on a thread provided on the vessel wall of the measuring cuvette, is suitable, in particular, for use as a fastening element.

The present invention will be explained in more detail below without limiting the general idea of the invention on the basis of exemplary embodiments, with reference to the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
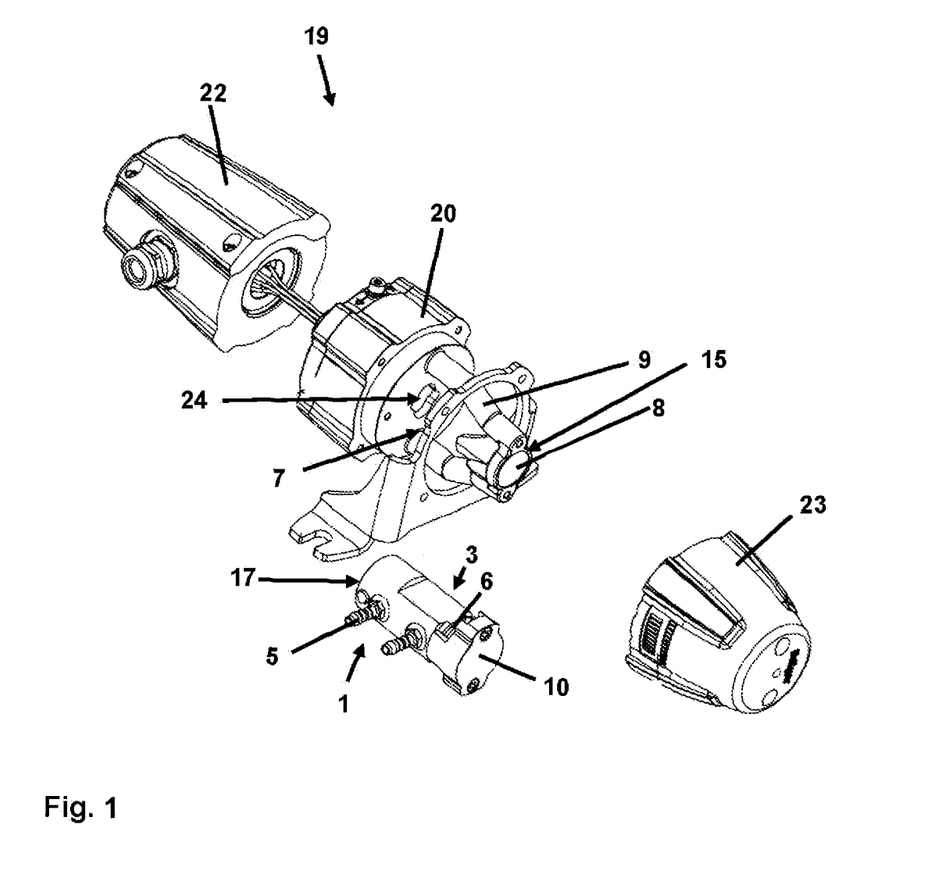
FIG. 1 is an exploded view of a gas-measuring device with a measuring cuvette.

Referring to the drawings, FIG. 1 shows an exploded view of a gas-measuring device 19 with the measuring cuvette 1 intended for installation. The gas-measuring device 19 shown is preferably used as a stationary gas-measuring device in plants of the pharmaceutical, chemical or petrochemical industry or in heating systems or power plants. The principal components of the gas-measuring device 19, namely, a housing part 22 for receiving the electronic system, a housing part 20, in which a radiation source as well as a detector are arranged, a bracket 8, to which a reflector is fastened and which has two legs 9, between which the mount 7 for fixing the measuring cuvette 1 is located, a cap 23, as well as the measuring cuvette 1 with the holding-down device 10 are shown.

A window 24 is provided in the outer wall of the housing part 20. The radiation emitted by the radiation source can exit the window 24 and radiation arriving from the sample chamber 3, during the operation, passes through before the arriving radiation falls on the detector.

Furthermore, a bracket 8 for receiving a mirror 15 is provided on the housing part 20. The mirror 15 is arranged on the side of the bracket 8 facing away from the housing part 20. The mount 7 for the measuring cuvette 1 is located between the two legs 9. The measuring cuvette 1 is inserted in this case such that the lower end of the measuring cuvette 1, which end has either an opening 17 towards the sample space 3 or a window element 27, is directed with a stop face 18 against a corresponding stop face of the housing part 20. An O-ring is inserted in this case as a sealing element 14 between the housing part 20 and the measuring cuvette 1 in order to seal the sample space 3 against the surrounding area. The holding-down device 10, which presses the measuring cuvette 1 against the housing part 20, having the radiation source and the detector, is fastened on the opposite side by means of two screws. The radiation source is an incandescent lamp, which emits a continuous radiation spectrum corresponding to an incandescent lamp temperature.

The measuring cuvette 1 is designed with a cylindrical housing wall 2 and has two hose connections 5, to which corresponding hoses for introducing and removing the process gas to be analyzed can be connected. The analysis of the process gas present in the sample space 3 of the measuring cuvette 1 takes place by directing infrared radiation from the radiation source in the housing part 20 through the sample space 3 onto a mirror 15 fastened to the bracket 8, from where the radiation is reflected and is directed again through the sample space 3 and finally falls on the detector likewise arranged in the housing part 20.

The radiation received by the detector is finally analyzed to determine how far or how much radiation was absorbed by the process gas within the sample space 3 in order to make it possible to obtain information on the species and/or composition of the process gas.

The measuring cuvette 1 is replaceable and is fixed during the operation in the mount 7 of the stationary gas-measuring device 8, which mount is provided therefor, between the two legs 9 of the bracket 8 by means of the holding-down device 10 fastened to the bracket 8.

Figure 2:
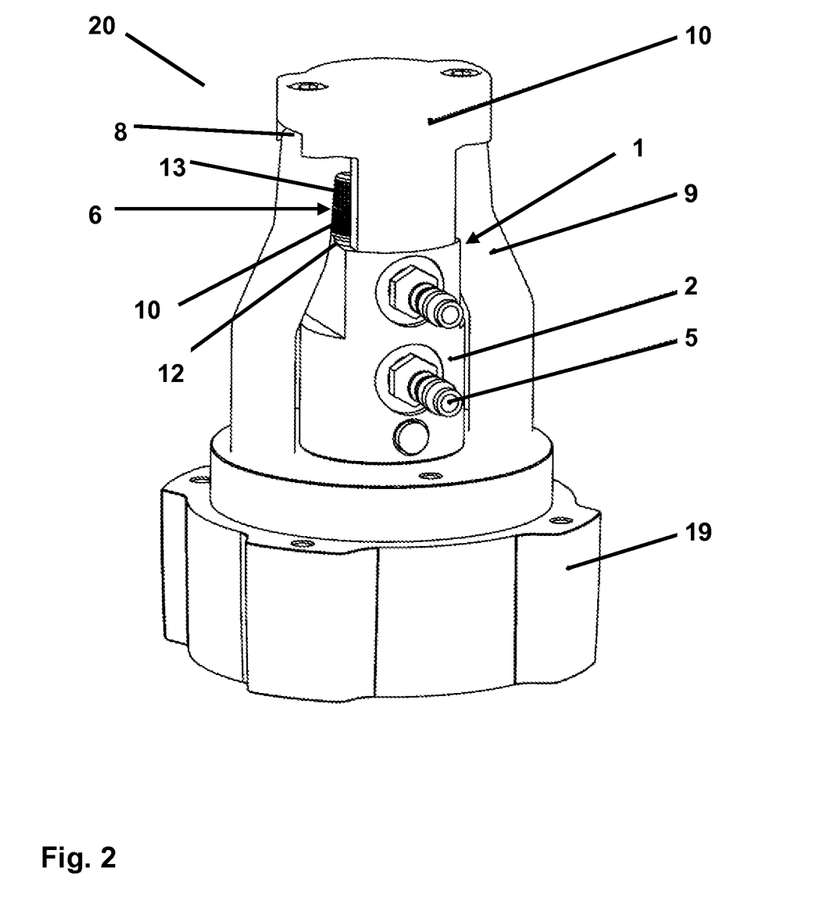
FIG. 2 is a housing part of a stationary gas-measuring device with a installed cuvette.

The measuring cuvette 1 is additionally shown in the mounted state in FIG. 2. The housing part 20 of a gas-measuring device 19, in which a radiation source as well as a detector are provided, is located under the measuring cuvette 1. Two legs 9 of a bracket 8, which carries in the upper area a reflector element 15, preferably a mirror or a reflection coating and in the interior space 7 of which the measuring cuvette 1 is accommodated between the legs 9, extend upwards from the housing part 20. The measuring cuvette 1 is fixed by means of the holding-down device 10 screwed tightly to the bracket 8 and is pressed lightly against the housing part 20 of the gas-measuring device 19 such that reliable sealing is guaranteed in this area between the sample space 3 of the measuring cuvette 1 and the surrounding area.

A screw cap 11 for fastening a window element 4, preferably a sapphire disk, is located on the vessel wall 2 of the cuvette 1 in the upper area of the measuring cuvette 1, the screw cap 11 provided as a fastening element 6 additionally having a height-adjustable adjusting element 13 in the form of a seal bonnet. This bonnet 13 is moved during the mounting relative to the measuring cuvette 1 such that secure sealing is achieved in the upper area between the seal bonnet 13 and the bracket 8 having the reflector 15 of the gas-measuring device 19.

Figure 3:
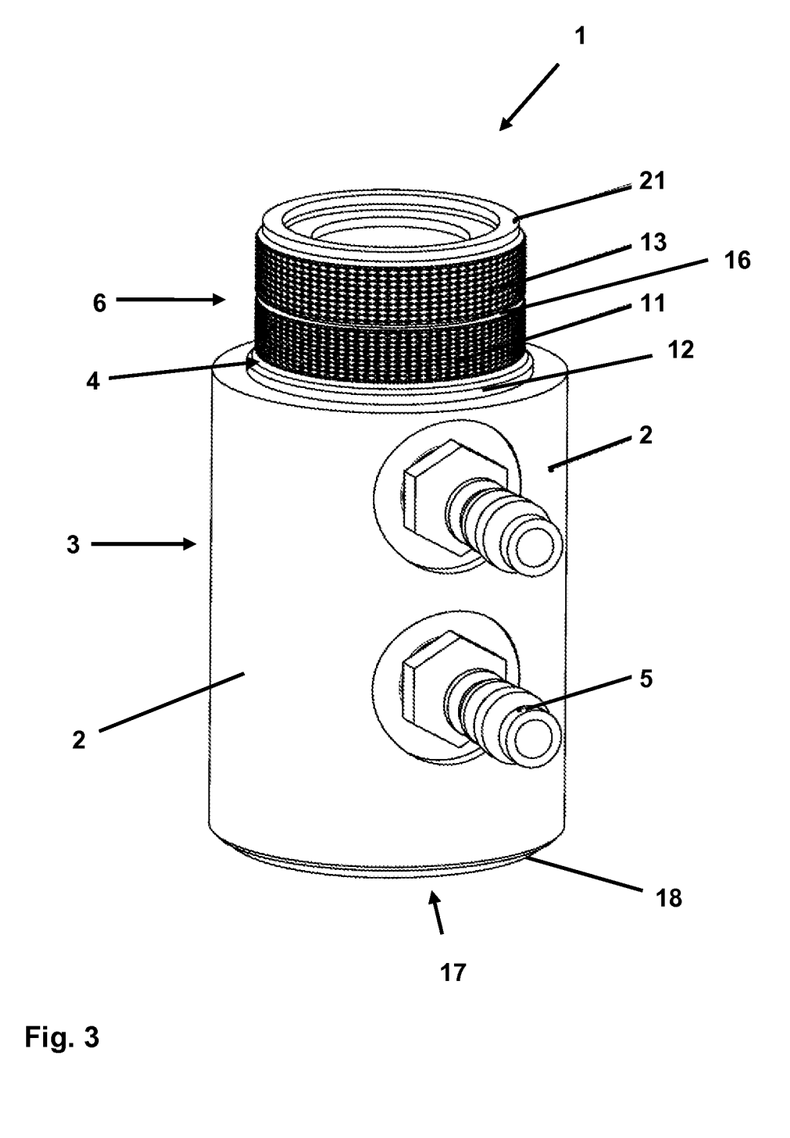
FIG. 3 is a cylindrical measuring cuvette with a fastening element designed according to the present invention.

FIG. 3 shows a measuring cuvette 1 designed according to the present invention, which has a cylindrically shaped housing wall 2. The housing wall 2 has two ports 5, which are used to admit and remove process gas and to which admission and discharge hoses can be fastened. A sample space 3, which is filled with process gas during the operation of the measuring cuvette 1 and which is half open downwardly, is located in the interior of the measuring cuvette 1. The lower, open end 17 of the measuring cuvette 1 is sealed with an O-ring 14 during the mounting of the process gas cuvette 1 against the top side of a stationary gas-measuring device.

An external thread 26, which is arranged according to the present invention on the housing wall 2 and to which a screw cap 11 is screwed as a fastening element 6, is located at the opposite, other end of the measuring cuvette 1. The thread 26 is usually a right-hand thread.

A sapphire disk is arranged as a window element 4 between the screw cap 11 and the housing wall 2 of the measuring cuvette 1. This sapphire disk is pressed onto the housing wall 2 of the measuring cuvette 1 by means of the screw cap 11 and thus fixed. To guarantee the necessary sealing, a sealing element 12 in the form of an O-ring, which is compressed by the pressure of the screw cap 11 onto the sapphire disk 4, is provided between the sapphire disk 4 and the housing wall 2. Furthermore, a seal bonnet, which is adjustable in height by means of an external thread located on the screw cap 11, is located as an adjusting element 13 on the screw cap 11 in the upper area. This thread as well as the seal bonnet 13 are provided with a left-hand thread in order to prevent the screw cap 11 from loosening when the seal bonnet 13 is tightened by force transmission by means of friction.

If the seal bonnet 13 is screwed upwards onto the surface of the mount 7, which surface is to be sealed, especially onto the surface of the bracket 8, a stationary gas-measuring device, the force applied for the screw cap 11 leads to tightening and to a further compression of the O-ring 12.

If the seal bonnet 13 is loosened, it reaches a stop 16 after a few turns and is blocked. The screw cap 11 and the seal bonnet 13 can then be unscrewed in no time. A flat packing is located as a sealing element 21 on the seal bonnet 13 in order to guarantee sealing between the seal bonnet 13 and the mount 7, especially between the seal bonnet 13 and the bracket 8 having the reflector 15, above the cuvette 1. The flat packing 21 has a free aperture in order to avoid undesired shadowing at the mirror 15.

On the one hand, reliable sealing can be ensured between the seal bonnet 13 and the bracket 8 having the reflector 15 by means of the height-adjustable seal bonnet 13 described, and, on the other hand, length tolerances of the mount, especially of the bracket 8, can be compensated in a simple manner.

When mounting the measuring cuvette 1, this is first inserted into the mount 7 between the legs 9 of the bracket 8, and the holding-down device 10 is fastened at the bracket 8 of the mount 7, and corresponding surfaces of the holding-down device 10 and of the housing wall 2 of the measuring cuvette 2 abut against one another, and the measuring cuvette 1 is pressed in the direction of the housing of the gas-measuring device 19 having the radiation source and the detector. The seal bonnet 13 arranged on the screw cap 11 is finally moved upwards by means of a screwing motion until reliable sealing is achieved between the seal bonnet 13 and the bracket 8 having the reflector. The flat packing 21 provided between the seal bonnet 13 and the bracket 8 is slightly compressed in the process.

Figure 4:
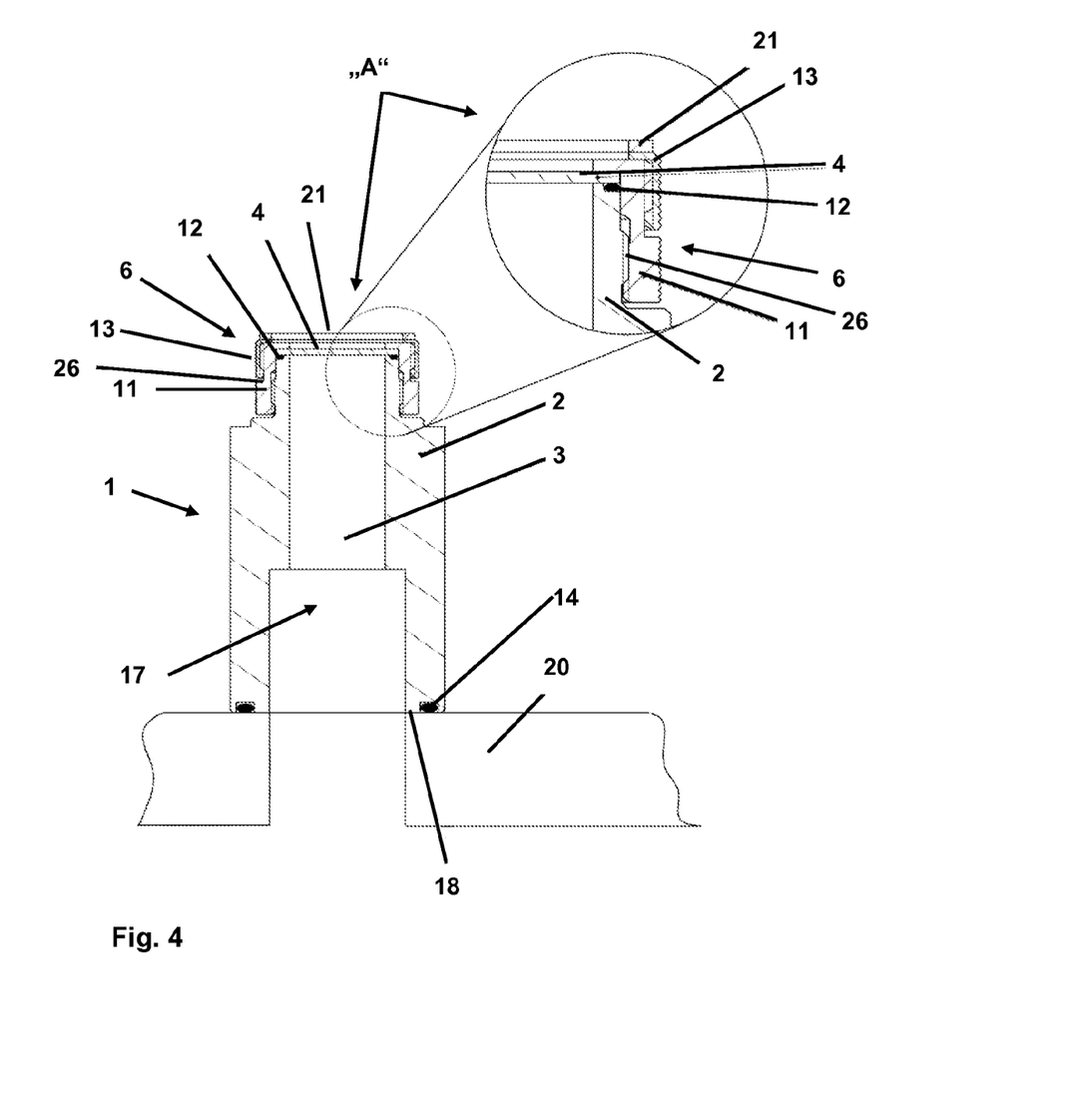
FIG. 4 is a sectional view of a half-open measuring cuvette designed according to the present invention.

FIG. 4 shows a sectional view through a measuring cuvette 1, which is placed on a housing part 20 of a gas-measuring device 19 having a radiation source and detector and is sealed by means of an O-ring 14. In the direction of the housing part 20 in which the radiation source and the detector are located, the measuring cuvette 1 has a half-open sample space 3 with a lower opening 17, which infrared radiation emitted by the radiation source can enter unhindered. An opening 24 tightly covered with a sapphire disk is provided for this in the housing part 20 of the gas-measuring device 19.

In its upper area, the housing wall 2 of the measuring cuvette 1 has an external thread 26, which is designed as a right-hand thread and onto which a screw cap 11 is screwed as a fastening element 6. A window element 4 in the form of a sapphire disk is fixed on the upper end of the housing wall 2 by means of the screw cap 11. To guarantee the necessary sealing in this area, an O-ring is clamped as a sealing element 12 between the sapphire disk 4 and the housing wall 2.

In addition, the screw cap 1 has, on its upper circumference, an external thread, which is designed as a left-hand thread in this case. A seal bonnet 13 is screwed, in turn, onto this left-hand thread for height adjustment and thus for adjusting the effective length of the measuring cuvette 1, i.e., the distance between the lower end facing the housing part 20 with the radiation source and the detector, and the opposite end of the measuring cuvette 1 facing the bracket 8 with the reflector 15.

Detail view "A" shows an enlarged view of the embodiment of the screw cap 11 screwed onto the housing wall 2 with the height-adjustable seal bonnet 13 screwed, in turn, thereon. This view also shows clearly how the seal 12 is clamped in between the sapphire disk 4 and the top end of the housing wall 2 and thus ensures reliable sealing of the sample space 3 against the surrounding area.

In the mounted state of the measuring cuvette 1 shown in FIG. 4 with the sample space 3 and a free internal diameter for receiving the process gas, this measuring cuvette 1 is seated on the surface of the housing part 20 having the radiation source and the detector of a stationary gas-measuring device. It is ensured in any case that the screw cap 11 used as a fastening element 6 including the seal bonnet 13 and seals 13, 21 make possible the free passage of the radiation through the interior space of these components, so that the ray path between the radiation source and the reflector 15, preferably mirror, or between the reflector element 15 and the detector is not shadowed.

Figure 5:
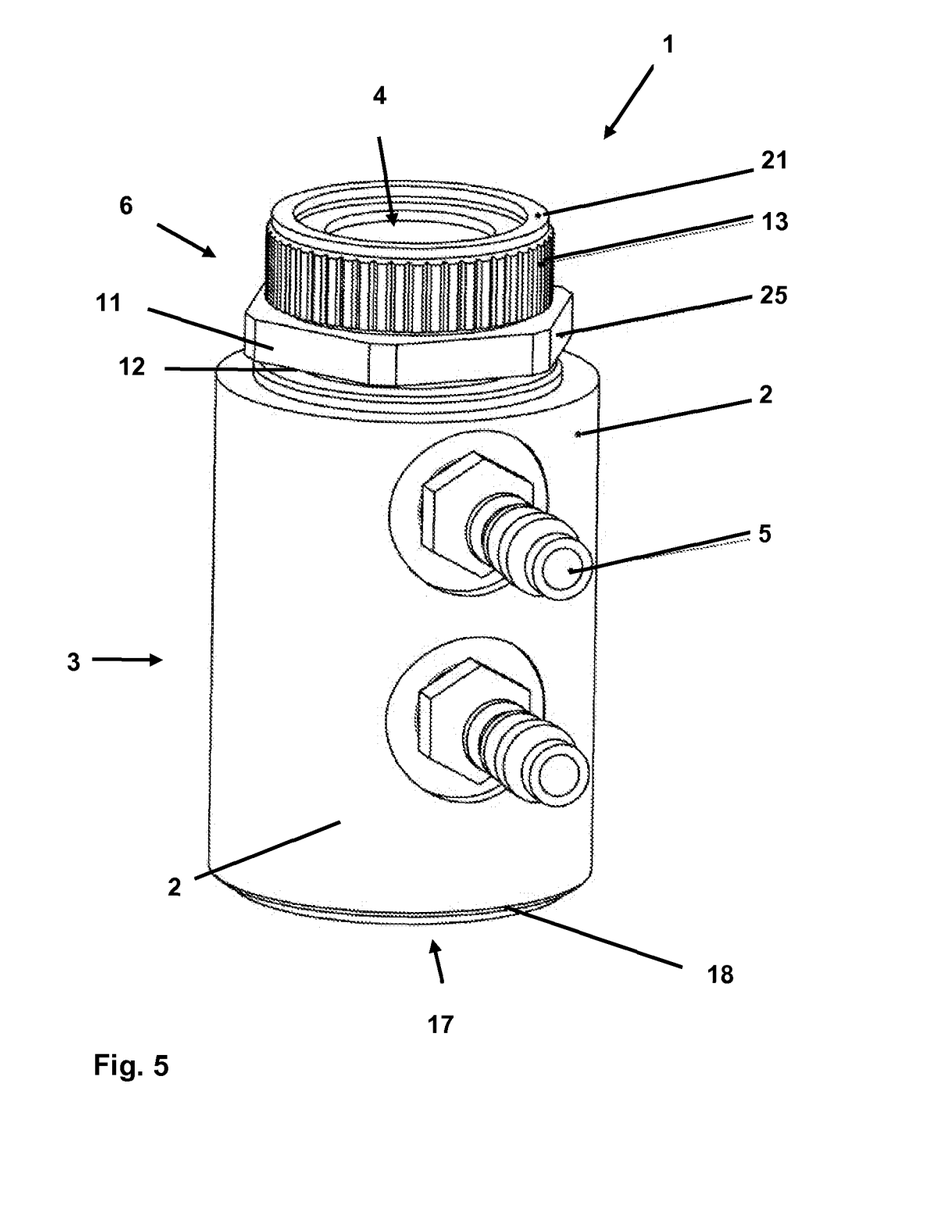
FIG. 5 is a measuring cuvette with a screw cap and connection element for an open-end wrench.

FIG. 5 shows a special embodiment of a measuring cuvette 1 designed according to the present invention. An essential feature is that the measuring cuvette 1 shown has a connection element 25 for an open-end wrench, so that simple tightening and loosening of the screw cap 11 is possible. By using suitable torque wrenches, it can be guaranteed in this connection that the screw cap 11 used as a fastening element 6 for the disk 4 is tightened with a defined torque in order to thus guarantee reliable sealing without the screw cap 11 becoming tightened excessively.

The height-adjustable seal bonnet 13 is screwed, in turn, onto the screw cap 11 by means of a left-hand thread and carries a flat packing 21. The screw cap 11 is first screwed onto the thread 26 of the housing wall 2 of the measuring cuvette 1 during mounting in order to thus hold and fix the sapphire disk 4 in the desired position. It is only then that the measuring cuvette 1 is fastened within the mount 1 of a gas-measuring device 19.

The process gas to be analyzed is admitted and removed via the respective connection elements 5 provided on the housing wall 2, especially hose connections.

Figure 6:
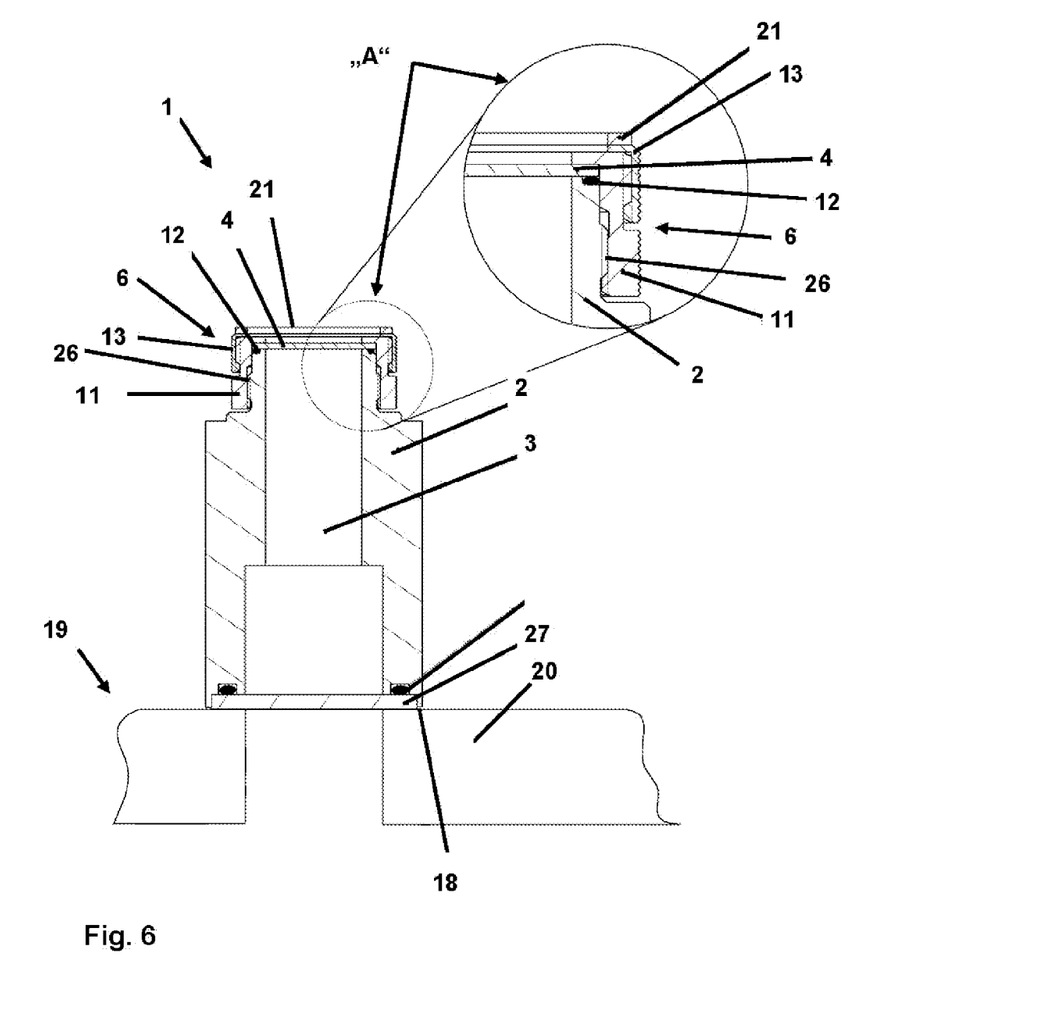
FIG. 6 is a sectional view of a measuring cuvette designed according to the present invention with screw cap and adjusting element for height adjustment.

Furthermore, FIG. 6 shows in a sectional view a measuring cuvette 1 designed according to the present invention, whose sample space 3 is not half open but has a second window element 27 in the form of a sapphire disk. This second window element 27 is arranged in the lower area facing the housing part 20 of a gas-measuring device 19 having a radiation source and a detector and is sealed by means of an O-ring 14. The upper area of the measuring cuvette 1 is designed, in turn, with a screw cap 11, which has, moreover, a height-adjustable seal bonnet 13.

The upper sapphire disk 4 as well as a seal 12 arranged between the sapphire disk 4 and the top end of the housing wall 2, especially in the form of an O-ring, is fixed reliably in the desired position by means of the screw cap 11 located in the upper area. The two sapphire disks 4, 27 used represent two optically transparent window elements, and the measuring cuvette 1 is, in turn, seated on one side on the surface of a housing part of a stationary gas-measuring device 19 having a radiation source and detector. The sample space 3 is defined in this case by a disk 4, 27 sealed with an O-ring 12, 14 both upwardly and downwardly. The lower sapphire disk is now pressed by the slight pressure generated by means of the holding-down device 10 against the stop face of the housing part 20.

However, it is also conceivable according to a special embodiment that fastening elements 6, preferably with a screw cap, are provided at both ends of the measuring cuvette 1 in order to fasten the disks 4 on the housing wall of the measuring cuvette 1. In any case, both disks 4, 27 are transparent to radiation in the spectral range relevant for the measurement, especially in the infrared range.

A height-adjustable seal bonnet 13, on which a flat packing 21 is, furthermore, arranged, is located, in turn, in the upper area of the screw cap 11. The flat packing 21 is used here to seal gaps that may develop above the measuring cuvette 1 between the measuring cuvette 1 and the bracket 8 of the cuvette mount 7 of the stationary gas-measuring device.

The lower O-ring 14 arranged on the side of the housing part with the radiation source and the detector is compressed by a pressing force, which is generated by means of a holding-down device 10. The needed pressing force is preferably generated in the upper area, in turn, by means of a height-adjustable seal bonnet 13 by this being moved in the direction of the bracket 8 having the reflector element 15 of the stationary gas-measuring device.

While specific embodiments of the invention have been shown and described in detail to illustrate the application of the principles of the invention, it will be understood that the invention may be embodied otherwise without departing from such principles.

APPENDIX

List of Reference Numbers

| | |
|---|---|
| 1 | Measuring cuvette |
| 2 | Vessel wall |
| 3 | Sample space |
| 4 | Window element |
| 5 | Inlet and outlet for the sample gas |
| 6 | Fastening element |
| 7 | Mount |
| 8 | Bracket |
| 9 | Bracket leg |
| 10 | Holding-down device |
| 11 | Screw cap |
| 12 | Sealing element between window element and housing wall |
| 13 | Adjusting element |
| 14 | Sealing element between housing wall and housing part |
| 15 | Reflector |
| 16 | Stop |
| 17 | Opening of the sample space |
| 18 | Stop face |
| 19 | Gas-measuring device |
| 20 | Housing part containing radiation source and detector |
| 21 | Sealing element between adjusting element and bracket |
| 22 | Housing part containing electronic system |
| 23 | Cap |
| 24 | Window in front of radiation source and detector |
| 25 | Connection element |
| 26 | External thread |
| 27 | Window opening in housing part |

What is claimed is:

1. A measuring cuvette for a spectroscopic analysis of a process gas sample arranged in the ray path between a radiation source and a detector, the measuring cuvette comprising:

a vessel wall, which at least partially encloses a sample space for receiving a process gas;

a window element, through which electromagnetic radiation can be coupled into the sample space from an outside and which is indirectly or directly connected with the vessel wall;

an inlet connection through which the process gas can be introduced into the sample space;

an outlet connection through which the process gas can be removed from the sample space; and an annular fastening element detachably connecting the window element with the vessel wall such that the window element can be separated from the vessel wall without destruction of the window element, the annular fastening element comprising a peripheral connection portion and defining an opening, through which the electromagnetic radiation falls on the window element, the annular fastening element further comprising an adjusting element connected to and forming a part of the fastening element for varying a distance between surfaces defining ends of the cuvette, which surfaces are located opposite each other in a longitudinal extension.

2. A measuring cuvette in accordance with claim 1, wherein the window element comprises a sapphire disk.

3. A measuring cuvette in accordance with claim 1, further comprising a sealing element between the window element and the vessel wall in the mounted state of the window element.

4. A measuring cuvette in accordance with claim 1, wherein the peripheral connection portion of the fastening element comprises at least one fastening element screw thread cooperating with a vessel wall screw thread.

5. A measuring cuvette in accordance with claim 4, wherein:

the fastening element comprises a screw cap with the fastening element screw thread provided as an inward screw thread which can be screwed onto the thread provided on an outer portion of the vessel wall wherein the fastening element further comprises an inner peripheral portion defining the opening and having a radial extent engaging an annular periphery of the window element, the inner peripheral portion cooperating with the vessel wall to form a clamping element, clamping the window element between the inner peripheral portion of the fastening element and the vessel wall.

6. A measuring cuvette in accordance with claim 5, wherein a packing ring is arranged between the screw cap and the window element in the mounted state of the window element.

7. A measuring cuvette in accordance with claim 1, further comprising a reflection device provided in the sample space for an at least partial reflection of electromagnetic radiation reaching it.

8. A measuring cuvette in accordance with claim 1, wherein the vessel wall has an essentially cylindrical design.

9. A measuring cuvette in accordance with claim 1, wherein the electromagnetic radiation passes through the sample space along a greatest extension of the measuring cuvette.

10. A measuring cuvette in accordance with claim 1, wherein the fastening element comprises a screw cap with the fastening element screw thread provided as an inward screw thread which can be screwed onto the thread provided on an outer portion of the vessel wall and an external thread and the adjusting element comprises an adjusting element annular end surface and an annular wall with an internal thread engaging the external thread for varying a distance between the adjusting element annular end surface and a longitudinal extension of the screw cap for varying the distance between surfaces defining the cuvette, which surfaces are located opposite each other in the longitudinal extension.

11. A measuring cuvette in accordance with claim 1, further comprising a sealing element wherein:

the vessel wall has a stop face as well as an opening between the sample space and the surrounding area; and the opening cooperates with the stop face to form a gas-measuring device with radiation source connection such that the opening, including the sealing element, sealed gas-tightly against an opening surrounding area and electromagnetic radiation is coupled into the sample space via the opening.

12. A gas-measuring device forming a gas detector, the gas-measuring device comprising:

a measuring cuvette comprising:

a vessel wall, which at least partially encloses a sample space for receiving a process gas, the vessel wall having an outer annular connection interface;

a window element, through which electromagnetic radiation can be coupled into the sample space from an outside and which is indirectly or directly connected with the vessel wall;

an inlet connection through which the process gas can be introduced into the sample space;

an outlet connection through which the process gas can be removed from the sample space; and an annular fastening element detachably connecting the window element with the vessel wall such that the window element can be separated from the vessel wall without destruction of the window element, the annular fastening element comprising a connection portion with an inward annular connection interface having an axial extent along the vessel wall and fixing the annular fastening element to the outer annular connection interface of the vessel wall to fix a position of the window element, the annular fastening element defining a radiation opening, through which the electromagnetic radiation falls on the window element, the fastening element further comprising an outward annular connection interface having an axial extent and an adjusting element comprising an adjusting element inward annular connection interface having an axial extent and an adjustment element end surface, a position of the adjusting element along the axial extent of the outward annular connection being varied to vary a position of the adjustment element end surface relative to the window element to adjust a distance between axial end surfaces defining an axial extent of the cuvette, which end surfaces are located opposite each other in the longitudinal extension, wherein the axial adjusting element end surface defines the axial end surface adjacent to the window element.

13. A gas-measuring device in accordance with claim 12, further comprising: a gas measuring device housing part having a radiation source and a bracket, wherein the measuring cuvette is fixed between the radiation source and the bracket.

14. A gas-measuring device in accordance with claim 13, further comprising a reflection device fastened at the bracket, the reflection device reflecting radiation exiting from the sample space partially in a direction of the sample space.

15. A gas-measuring device in accordance with claim 13, further comprising a sealing element between the window element and the vessel wall in the mounted state of the window element, wherein:

the fastening element comprises an inner peripheral portion defining the opening and having a radial extent engaging an annular periphery of the window element, the inner peripheral portion cooperating with vessel wall to form a clamping element, clamping the window element between the inner peripheral portion of the fastening element and the vessel wall.

16. A gas-measuring device in accordance with claim 13, wherein:

the outer annular connection interface comprises an outer screw thread provided on the vessel wall; and the fastening element comprises a screw cap and the inward annular connection interface comprises an inner thread which can be screwed onto the outer thread provided on the vessel wall.

17. A gas-measuring device in accordance with claim 13, wherein the fastening element comprises a screw cap and the inward annular connection interface comprises an inner thread to screw onto the outer thread provided on the vessel wall and the outward annular connection interface comprises and outer thread and the adjusting element comprises an adjusting element cap defining the adjusting element end surface and the adjusting element inward annular connection interface comprises an inner thread connected to the annular fastening element and varying a distance between axial end surfaces defining an axial extent of the cuvette, which surfaces are located opposite each other in the longitudinal extension, wherein the axial adjusting element defines the one of the axial end surfaces adjacent to the window element.

18. A gas-measuring device in accordance with claim 13, further comprising a sealing element wherein:

the vessel wall has a stop face as well as an opening between the sample space and the surrounding area;

the opening cooperating with the stop face to form a gas-measuring device with radiation source connection such that the opening including the sealing is element sealed gas-tightly against an opening surrounding area and electromagnetic radiation is coupled into the sample space via the opening.

19. A gas-measuring device forming a gas detector, the gas-measuring device comprising:

a measuring cuvette comprising:

a vessel wall, which at least partially encloses a sample space for receiving a process gas, the vessel wall having an outer annular connection interface comprising an outer screw thread provided on the vessel wall;

a window element, through which electromagnetic radiation can be coupled into the sample space from an outside and which is indirectly or directly connected with the vessel wall;

an inlet connection through which the process gas can be introduced into the sample space;

an outlet connection through which the process gas can be removed from the sample space;

an annular fastening element comprising a screw cap comprising an outer peripheral connection portion with an inward annular connection interface having an axial extent along the vessel wall and comprising an inner thread fixing the annular fastening element to the outer screw thread of the vessel wall, the annular fastening element further comprising an annular inner peripheral cap portion defining a radiation opening, through which the electromagnetic radiation falls on the window element, the annular inner peripheral cap portion having a radial extent engaging an annular periphery of the window element, the inner peripheral cap portion cooperating with vessel wall to form a clamping element, clamping the window element between the inner peripheral cap portion of the fastening element and the vessel wall, the annular fastening element detachably connecting the window element with the vessel wall such that the window element can be separated from the vessel wall without destruction of the window element; and an axial adjusting element with an adjusting element end surface, wherein:

the annular fastening element further comprises an outer adjusting interface thread;

the axial adjusting element comprises an inner adjusting interface thread;

the outer adjusting interface thread cooperates with the inner adjusting interface thread to form a position adjustment connection interface;

the axial adjusting element is connected to the annular fastening element by the position adjustment connection interface to position the axial adjusting element end surface, as a cuvette end surface, opposite another cuvette end surface;

the adjusting element end surface and the other cuvette end surface define an axial extent of the cuvette; and rotation of the connected axial adjusting element relative to the connected annular fastening element varies a distance between the adjusting element end surface and the window element and to adjust a position of the axial adjusting element end surface and the other cuvette end surface to vary the axial extent of the cuvette.

20. A gas-measuring device in accordance with claim 19, wherein:

the end surface of the adjusting element is adjacent to the window element and defines a radiation opening, through which the electromagnetic radiation falls on the window element.

* * * * *